United States Patent [19]

Foster et al.

[11] 4,088,025

[45] May 9, 1978

[54] MATERIAL SAMPLING APPARATUS

[75] Inventors: Bill D. Foster, Ankeny; John T. Comiskey, Johnston; LeRoy H. Degner, Des Moines, all of Iowa

[73] Assignee: Elevator Contractors, Inc., Des Moines, Iowa

[21] Appl. No.: 806,737

[22] Filed: Jun. 15, 1977

[51] Int. Cl.² ............................................... G01N 1/10
[52] U.S. Cl. .................................................. 73/423 R
[58] Field of Search ........................... 73/425.2, 423 R

[56] References Cited

U.S. PATENT DOCUMENTS

| 170,545 | 11/1875 | Gard et al. | 73/452.2 |
|---|---|---|---|
| 1,256,413 | 2/1918 | Wiswell | 73/425.2 |
| 3,789,671 | 2/1974 | Larson | 73/423 R |

*Primary Examiner*—S. Clement Swisher

*Attorney, Agent, or Firm*—Henderson, Strom, Sturm, Cepican & Fix

[57] ABSTRACT

A device for collecting and removing samples by vacuum suction created in a tube with an opening at the bottom. The opening communicates with a connecting chamber that separates the vacuum tube fron two tubes, one inside the other, used to gather the required sample. An orifice permitting a jet of air to cross the connecting chamber and enter the vacuum tube aids in removing the sample from the two tubes. Angled partitions inside the inner tube aid in dumping the sample through aligned openings in the two tubes into the connecting chamber. The tubes are kept at a desired angle when inserted by a spring assembly. The spring assembly also allows break-away movement should the device hit an obstacle.

14 Claims, 8 Drawing Figures

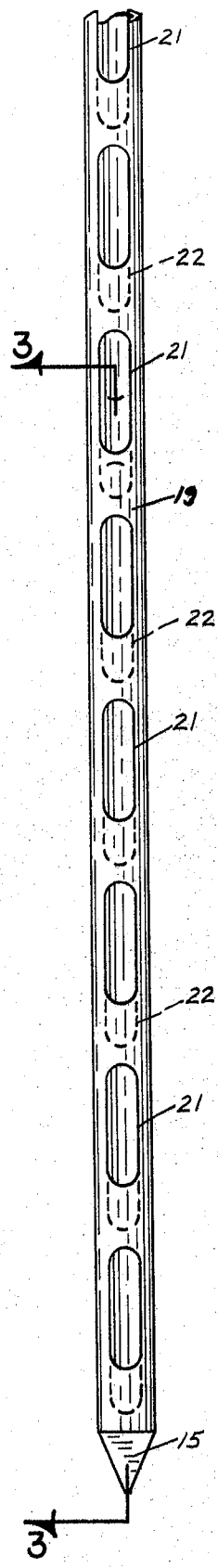
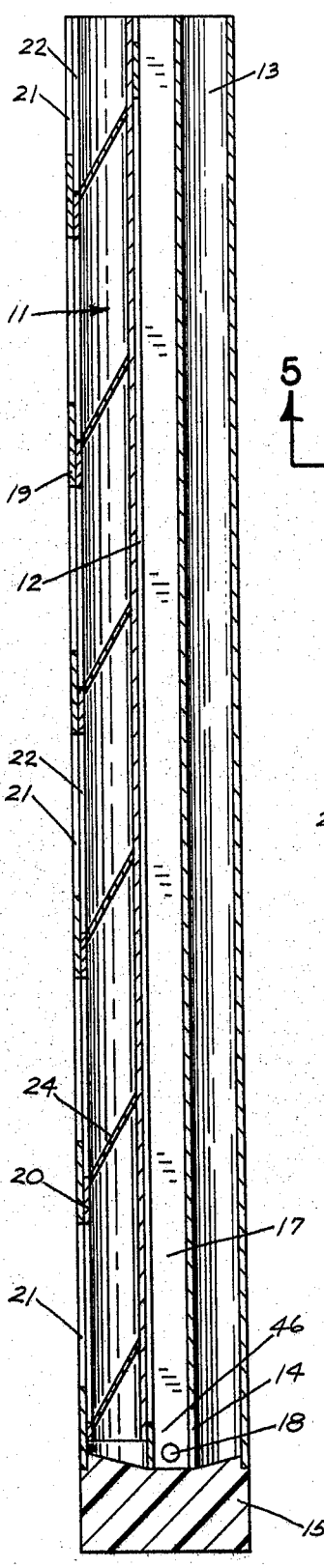
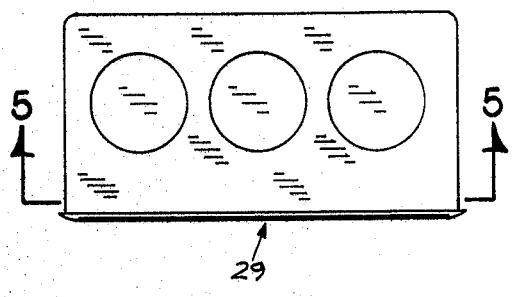
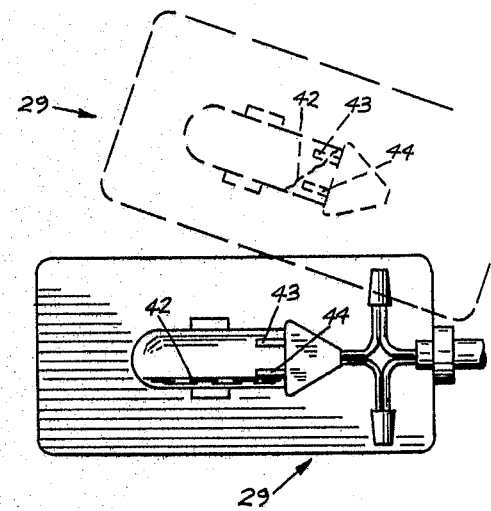

MATERIAL SAMPLING APPARATUS

BACKGROUND OF THE INVENTION

This invention relates to sample probe devices. When large amounts of material are marketed, particularly grain, it is desirable to remove a representative sample for analysis. Previously, a hand held probe was manually inserted into the bulk of material. This manual sampling was slow, tedious and tiring for the operator to insert the probe to the full, proper depth. The present invention allows an operator to insert the probe using power assisted machinery from a remote location and receive the sample at that remote location, preferably near the sample analysis equipment.

Previously used power assisted sample probe devices suffered from numerous problems. The probe head, when being inserted into the material to be sampled, sometimes struck an obstacle or the side of the bulk container transporting the material. The lack of a break-away device allowing the probe freedom of movement sometimes resulted in damage to the probe or bulk container or both.

Additional problems arose when the previously used sample probe devices tried to remove the sample taken by vacuum. The vacuum was applied to the entire sample column all at once. Sometimes, instead of drawing the sample out, the vacuum suction tended to pull on the entire column. This caused the sample column to become packed, which required clearing of the jam.

Finally, the previously used sample probe devices, for example as shown in U.S. Pat. No. 3,789,671 to Larson, often had one or very few openings to bring sample material into the probe. Such probes also took samples as it moved through the bulk of the material. The result often was an unrepresentative sample with too many fines of sample material, especially since fines are lighter and more easily moved by vacuum than heavier kernels of grain.

SUMMARY OF THE INVENTION

This invention relates to a sampling device having a part that receives a sample of material and a part with an outlet. A vacuum tube on one side of the device has an opening at the bottom thereof. The vacuum tube is connected to a device that creates a negative pressure in the vacuum tube. A connecting chamber connects the sample receiving device outlet with the vacuum tube opening. A part, usually containing an orifice, is connected to the sample receiving part, such part permits air to enter the connecting chamber in such a way that a jet of air is formed under the opening in the sample receiving part. This jet of air helps the material in the sample receiving part to move into the vacuum tube. The sample receiving part is preferably made of two tubes, one inside the other, both tubes having openings therein that in one position communicate such that sample material may travel through the openings. Inside the inner tube, angled partitions run from the opening upwardly to the opposite wall. The angled partitions facilitate removal of the sample material.

It is an object of the invention to provide a sample probe device that has an orifice near the probe head that, in conjunction with a vacuum tube, directs a jet of air across the holding chamber into the vacuum tube, thus assisting in removing the sample from the probe to a remote location.

Another object of the present invention is the provision of angled members dividing the sampling tube into compartments to provide easy and sure removal of the sample once taken from the bulk of the material.

Another object of the present invention is the provision of a holding chamber to receive the sample from the sampling tube before sucking the sample away in a vacuum tube.

A still further object of the present invention is the provision of a mechanism for inserting and withdrawing the probe tubes and head and allowing a break-away freedom of movement in cash the probe should hit an obstacle or side of the bulk container transporting the material.

Another object of the present invention is to provide a device capable of delivering a representative sample of bulk material to a remote location without the operator leaving that remote location.

Other objects, advantages and novel features of the present invention will become apparent from the following detailed description of the invention when considered in conjunction with the accompanying drawings.

BRIEF DESCRIPTION OF THE DRAWINGS

FIG. 2 is a detailed, enlarged front perspective view of the sample probe tubes and receiving chamber;

FIG. 3 is a vertical cross-sectional view taken along lines 3—3 of FIG. 2;

FIG. 4 is a view of the vacuum control switch taken along lines 4—4 of FIG. 1;

FIG. 5 is a cross-sectional view of the vacuum control switch taken along lines 5—5 of FIG. 4;

DESCRIPTION OF THE PREFERRED EMBODIMENT

Figure 1:
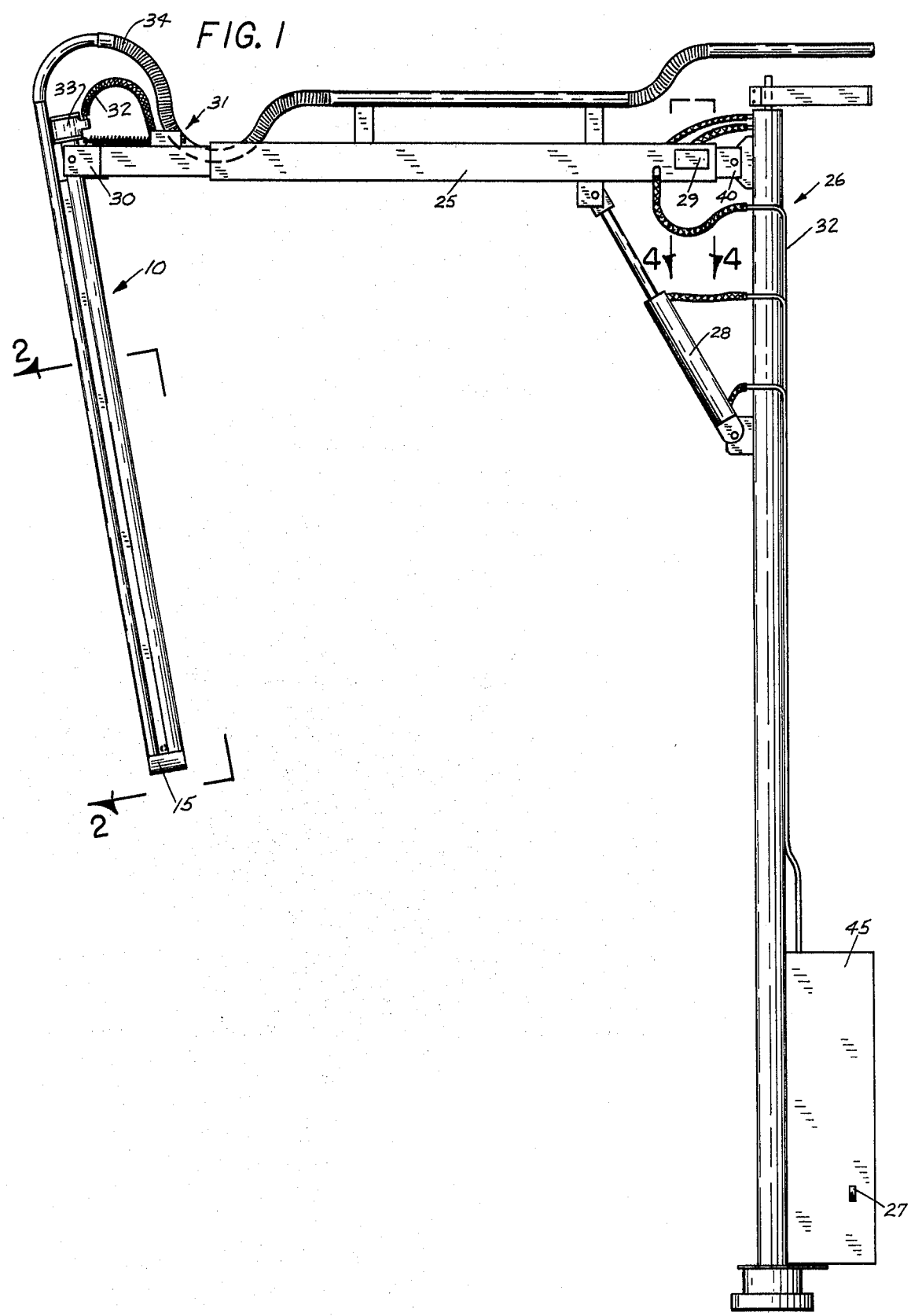
FIG. 1 is a perspective view of a sample probe device shown with a boom attached to a mounting base that contains hydraulic actuating equipment.

Referring now to the drawings wherein like reference numerals designate identical or corresponding parts throughout the several views, FIG. 1 shows a grain probe 10 mounted on a support structure including a boom 25 and support post 26.

The grain probe 10 is shown more particularly in FIGS. 2 and 3. On one side of the grain probe 10 there is a sampling device 11 which is comprised primarily of a first our outer tube 19 and a second or inside tube 20. The outside tube 19 has a plurality of inlet openings 21 on one side thereof and a large outlet opening 12 on the opposite side thereof. The second or inside tube 20 has a plurality of ports 22 disposed in one side thereof and a plurality of partitions 24 between each of the ports 22. These partitions 24 are generally elliptical in shape and span the inside of the tube 20. The partitions 24 extend at an angle from the inside wall of the second or inside tube 20 just below the bottom of the ports 22 upwardly to the opposite inside wall of the second or inside tube 20.

A sample receiving chamber 17 is connected to the sampling device 11 and a vacuum tube 13 is connected adjacent to the sample receiving chamber 17. At the lower portion of the vacuum tube 13 is an opening 14 for allowing communication between the vacuum tube 13 and the lowermost part of the sample receiving chamber, which chamber will be referred to as the connecting chamber 46. This connecting chamber 46 has an opening 18 therein which leads to the exterior of these tubes for allowing atmospheric air to enter, as will be described below. A wedge-shaped grain probe 15 is connected to the bottom of the grain probe device 10 as is clearly shown in FIGS. 1–3.

Referring again to FIG. 1, it can be seen that the grain probe 10 is pivotally mounted to the top of the boom 25 by means of a clevis and pin arrangement 30. A spring biasing assembly 31 is utilized in order to maintain the probe 10 at the desired angle for example at 10° from the vertical as is shown approximately in FIG. 1. The boom 25 has a hydraulic cylinder (not shown) therein and for the purpose of allowing the boom 25 to be adjustable in length. This also accounts for the reason that the vacuum tube hose 34 is loose; that is, to accommodate lengthening and shortening of the boom 25. The looseness of the hose 34 also allows pivoting of the grain probe 10.

A support post assembly 26 is connected to the ground or to the side of a building for the purpose of pivotally mounting the boom 25 thereto. This upstanding post assembly 26 is also rotatable about its longitudinal axis by an actuating mechanism such as hydraulic controls 45, although it is to be understood that other means for selectively pivoting the upstanding post assembly 26 and thereby the boom 25 and the grain probe 10 is fully equivalent thereto. A switch 27 on the upstanding post assembly 36 allows the operator to shut off the machinery without fear of its activation from remote controls. The pivotal connection of the post 26 to the boom 25 is made by a clevis and pin structure 40. A double-acting hydraulic cylinder 28 is utilized to pivot the boom 25 with respect to the upstanding post 26.

Figure 6:
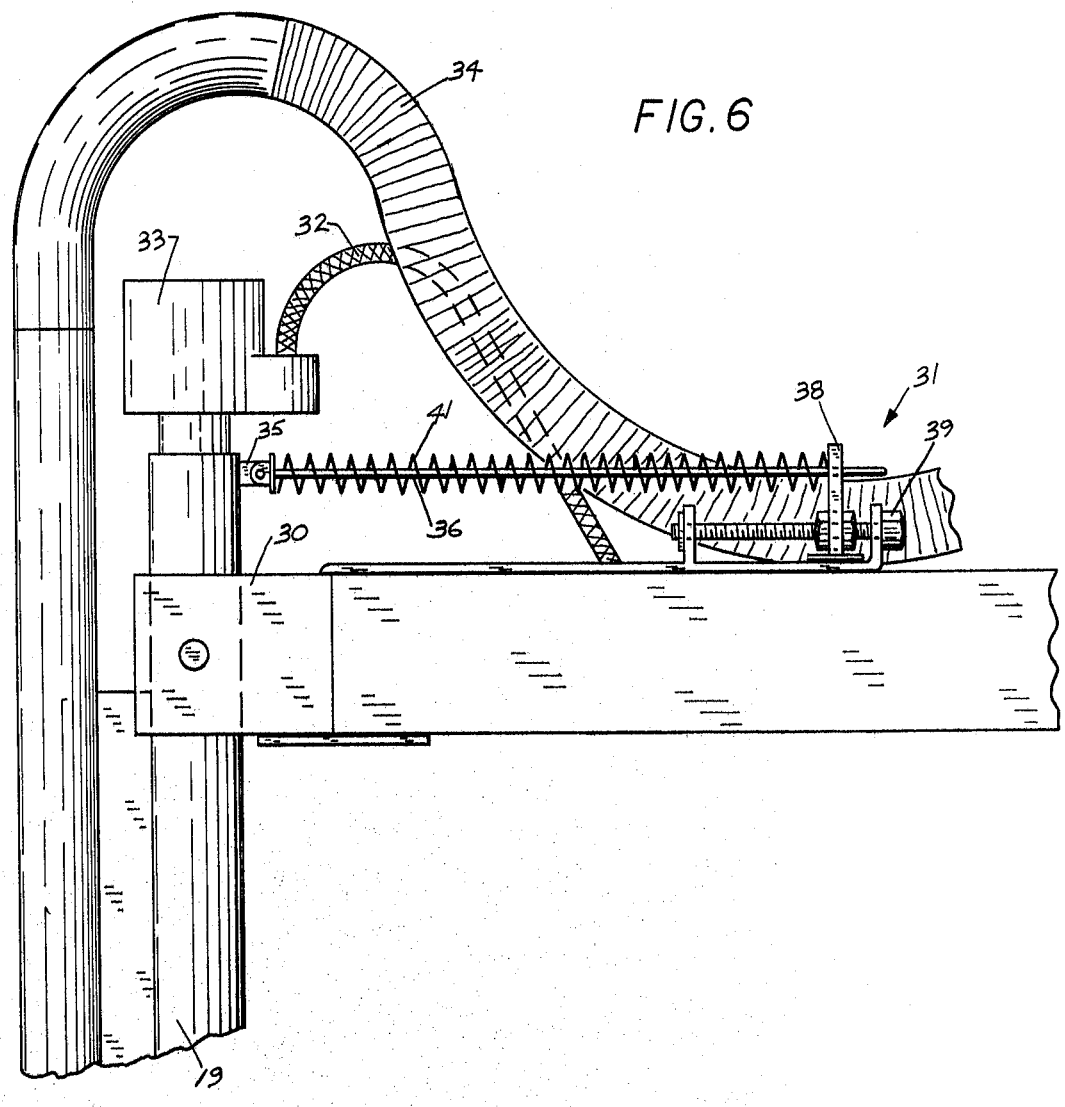
FIG. 6 is a detailed, enlarged perspective view of the outer boom end pivotally attached to the sample probe tubes and a spring assembly break-away device.
Figure 7:
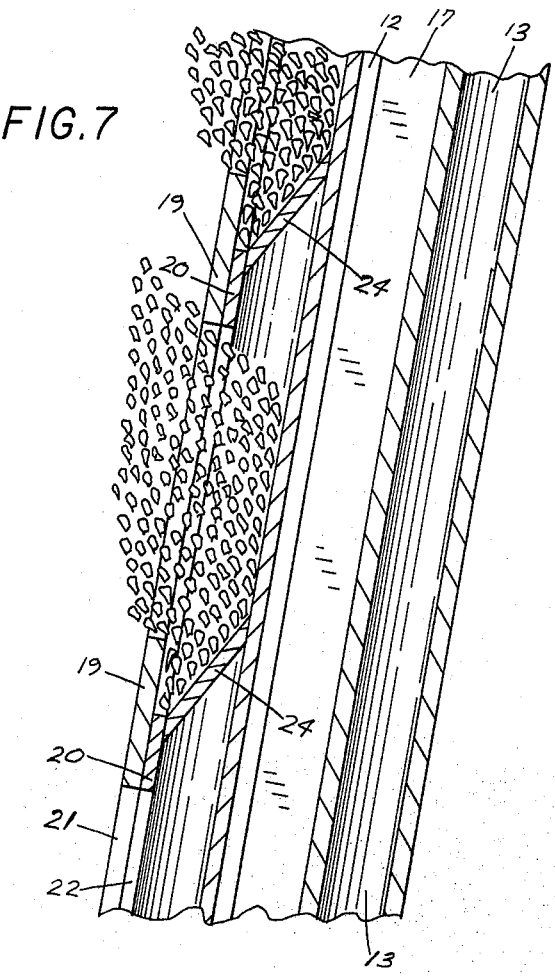
FIG. 7 is a partial cross-sectional view of the grain probe showing corn being sampled by the sampling device.

Referring now to FIG. 6, it is noted that the spring assembly 31 is pivotally mounted to the outer tube 19 of the grain probe 10 by means of a pivotal connection 35. A shaft 36 is specifically the portion of the spring assembly 31 which is pivotally connected to the grain probe 10. The other end of this shaft 36 extends through an opening in a bracket 38. The bracket 38 is adjustably attached to the boom 25 by means of a nut and bolt adjusting mechanism 39, which is clearly shown in FIG. 6. Rotation of the bolt 39 in one direction causes the bracket 38 to move to the left with respect to the boom 25 and rotation of the bolt 39 in an opposite direction causes the bracket 38 to move to the right with respect to the boom 25 as viewed in FIG. 6. A spring 41, preferably of a compression type, is disposed between the pivotal connection 35 and the bracket 38. In its preferred form, the ends of the spring 41 are secured to the connection 35 and bracket 38 such that the spring 41 would act as either a compression or a tension spring and thereby would tend to allow pivoting of the probe 10 in either direction should it happen to strike an obstruction or the container wall of the grain or the material to be sampled during insertion thereof into the sample. The rest of the time the probe 10 is held in its desired position, e.g., at 10° with respect to vertical. It is this spring assembly bolt 39 which is used to adjust the desired testing angle of the probe 10.

Referring now to FIGS. 1, 4 and 5, it can be seen that a mercury switch 29 is connected to the boom 25. This mercury switch is in the position shown in solid lines in FIG. 5 when the grain probe structure is in the position shown in FIG. 1. When the hydraulic cylinder 28 is lengthened in its effective length so as to pivot the boom 25 upwardly, however, the mercury switch moves to the position shown in dashed lines in FIG. 5, and the mercury 42 also flows from the position shown in solid lines in FIG. 5 to the position shown in dashed lines in FIG. 5, such that the mercury 42 completes an electrical connection between the two contacts 43 and 44. Once this electrical connection is made, this activates a vacuum pump (not shown) which causes a vacuum or negative pressure in the tube 34 and ultimately into the vacuum tube 13 of the probe 10.

In operation, a truck or trailer full of grain or other material would be ready to pull up to a station equipped with the invention shown in FIG. 1. Before the truck or trailer would pull up to such device, however, the hydraulic cylinder 28 would be activated such that the boom 25 and thereby the grain probe 10 would be in an elevated position. Normally, the grain probe device of this invention would remain in this elevated position in readiness to obtain a sample of material when not in use.

Figure 8:
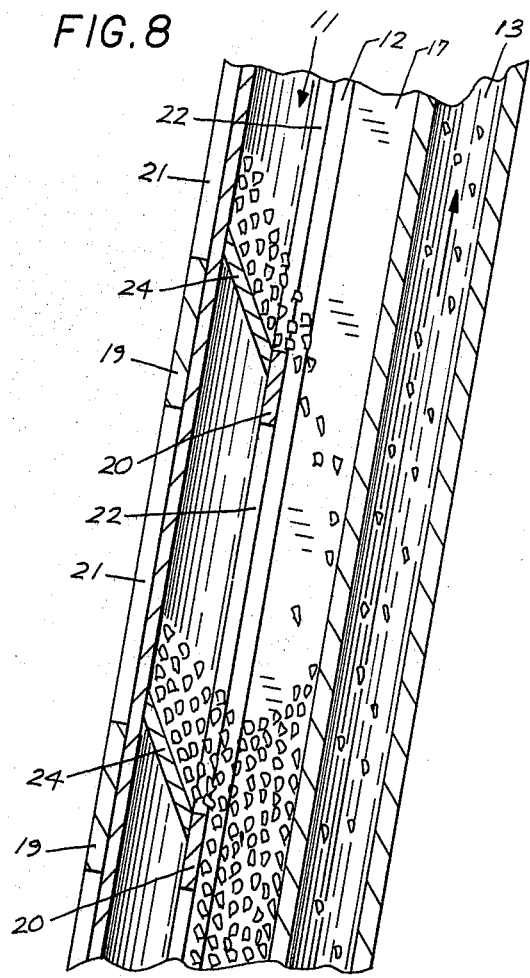
FIG. 8 is a partial cross-sectional view of the grain probe showing such corn being transferred to a sample receiving chamber.

Once the container full of material, such as cereal grains, is moved underneath the probe 10 in its elevated position, controls are activated to shorten the effective length of the hydraulic cylinder 28 such that the boom 25 and the sampling probe 10 move to the position shown in FIG. 1. At the time that the probe 10 is inserted into the material to be sampled, the second or inside tube 20 is in a position turned 180° from the position shown in FIG. 3, such that the openings 21 in the first or outer tube 19 are closed. Once the sample is ready to be taken, a rotary hydraulic motor 33 connected to the second or inside tube 20 is activated to rotate the tube 20 to the position shown in FIG. 3. Once this is done, the grain or other material to be sampled will flow into the grain sampling device 11 between the partitions 24. Once enough time has been allowed for these spaces to become full of material, the hydraulic motor 33 is again activated in order to rotate the inside tube 20 180°, to the position shown in FIG. 8. When this is done, the material slides smoothly down over the angled top surfaces of the partitions 24 and into the receiving chamber 17. The controls are then activated on the hydraulic cylinder 28 in order to lift the grain probe out of the material being sampled by increasing the effective length of the hydraulic cylinder 28 and pivoting the boom 25 upwardly. When this is done, the mercury switch shown in FIGS. 1, 4 and 5 is moved from the position shown in solid lines in FIG. 5 to the position shown in dashed lines in FIG. 5, thereby completing the electrical connection between the contact points 43 and 44. This, as referred to above, activates a vacuum pump connected to the tube 34, which causes a suction or negative pressure in the suction tube 13, thereby tending to pull the grain out of the receiving chamber 17.

It is very important to have an opening such as the opening 18 in the connecting chamber 46. The importance of this opening 18 is to create a jet of air which is pulled in through the opening 18 and across and up through the suction tube 13, thereby pulling the lowermost portions of the sample in the sample receiving chamber 17 along with it. This is to be distinguished from prior art vacuum sampling devices which do not have such an opening 18 and which tend to try to pull an entire column of material, such as a column full of material 17. Since this is very difficult, the column of material merely becomes packed and the device becomes inoperative.

In the present invention, the sample of material such as corn or other grain is sucked up through the vacuum tube 13 into the tube 34 and ultimately to a point, normally inside of a building, where testing facilities and equipment are readily available.

If it should happen that the material holding container, such as a truck, would pull away before the probe 10 is removed from the container, the probe 10 and boom 25 would rotate with the post 26 until the boom 25 would be pointing generally in the direction of movement of the truck. Upon continued movement of the truck in the same direction, the probe 10 would pivot upwardly (clockwise as viewed from FIG. 1), overcoming the compression bias of the spring 41 (FIG. 6), so that the probe will slide out of such truck box without being damaged.

Consequently, it can be seen that the present invention does indeed accomplish the objects set forth above. Obviously, many modifications and variations of the present invention are possible in light of the above teachings. It is therefore to be understood that, within the scope of the appended claims, the invention may be practiced otherwise than as specifically described.

We claim:

1. Apparatus comprising:
   means for receiving a sample of material, said receiving means having an outlet;
   a vacuum tube on one side of said sampling device, said vacuum tube having an opening at the bottom thereof;
   vacuum means connected to said vacuum tube for creating a negative pressure in said vacuum tube;
   connecting chamber means for connecting the receiving means outlet with said vacuum tube opening; and
   means connected to said receiving means below said receiving means opening for permitting air to enter said connecting chamber means whereby a jet of air is formed under the outlet in said receiving means and traverses said connecting chamber means to the vacuum tube causing material in said receiving means to be drawn into said vacuum tube.

2. The apparatus of claim 1 wherein said device includes sampling means for delivering a sample of material to said receiving means.

3. The apparatus of claim 2 wherein said sampling means comprises:
   a first tube having at least one opening in one side thereof; and
   a second tube disposed within said first tube, a port formed in said second tube, said second tube having a first position whereby said port is in communication with the opening in said first tube and a second position whereby said port is not in communication with the opening in said first tube, and a partition connected to the interior of said second tube, said partition having an angled surface that extends from the inside wall of the second tube just below the bottom of said port in said second tube upwardly to the opposite inside wall of said second tube.

4. Apparatus as described in claim 3 including means for rotating said second tubes between said first and said second positions.

5. The apparatus of claim 3 including:
   a second opening in said first tube;
   a second port disposed in said second tube and a second partition connected to said second tube, said second partition having an angled surface thereon that extends from the inside wall of said second tube just below the bottom of said second port, upwardly to the opposite inside wall of said second tube.

6. The apparatus of claim 3 wherein said first tube contains an opening in one side whereby said opening in said one side is in communication with said port of said second tube when said second tube is in said second position.

7. The apparatus of claim 6 including at least one opening on the back side of said first tube in communication with the port in the second tube when second tube is in said second position for emptying the sample of material through said opening in the back side of the first tube.

8. The sampling device of claim 7 further comprises:
   a boom pivotally attached to the top of said first tube at one end thereof;
   means connected to the other end of said boom for pivoting said boom so that said tubes are selectively inserted and withdrawn from the sample; and
   a spring assembly means mounted on said boom for maintaining a desired angle of said tubes upon insertion into a sample comprising a shaft pivotally connected at one end to the said first tube, a bracket connected to said boom, the other end of the shaft being slidably received in said bracket and adjustment means for controlling the position of said bracket with respect to said boom, thereby controlling angle of insertion of said tubes into sample.

9. The apparatus of claim 8 including switch means attached to said boom for activating and deactivating said vacuum means depending on the angle said boom is at in relationship to the ground.

10. A sampling device comprising:
    a first tube having at least one opening in one side thereof;
    a second tube disposed within said first tube, a port formed in said second tube, said second tube having a first position with respect to said first tube whereby said port is in comunication with the opening in said first tube and a second position whereby said port is not in communication with the opening in said first tube, and a partition connected to said second tube, said partition having an angled surface thereon that extends from the inside wall of said second tube below the bottom of said port in said second tube, upwardly to the opposite inside wall of said second tube;
    an opening disposed in the other side of said first tube whereby said opening in said other side of the first tube is in communication with said port of said second tube when the second tube is in said second position;
    a vacuum tube connected to said sampling device and having an opening therein;

vacuum means connected to said vacuum tube for creating a less than atmospheric pressure in said vacuum tube;

means for receiving a sample of material from said sampling device; and connecting chamber means for connecting the receiving means with said vacuum tube opening.

11. The sampling device of claim 10 including:

a second opening in said one side of said first tube;

a second port disposed in said second tube and a second participation connected to said second tube, said second partition having an angled surface thereon that extends from the inside wall of said second tube just below the bottom of said second port, upwardly to the opposite inside wall of said second tube.

12. The sampling device of claim 10 including means connected to said second tube for rotating said second tube between said first and second positions thereof.

13. Apparatus comprising:

sampling means for taking a sample from a container of granular material;

means for transferring said sample from said sampling means into a receiving chamber;

a tube connected to said receiving chamber; and pneumatic means for removing said sample from said receiving chamber through said tube.

14. Apparatus as defined in claim 13 wherein said pneumatic means comprises a vacuum means for creating less than atmospheric pressure in said tube.

* * * * *

Notice of Adverse Decision in Interference

In Interference No. 100,251, involving Patent No. 4,088,025, B. D. Foster, J. T. Comiskey and L. H. Degner, MATERIAL SAMPLING APPARATUS, final judgment adverse to the patentees was rendered Oct. 23, 1980, as to claims 10-14.

[*Official Gazette February 24, 1981.*]